United States Patent
Yang et al.

(10) Patent No.: US 11,206,987 B2
(45) Date of Patent: Dec. 28, 2021

(54) METHOD AND APPARATUS FOR CONCURRENT IMAGING AT VISIBLE AND INFRARED WAVELENGTHS

(71) Applicant: SUZHOU CARING MEDICAL CO. LTD., Suzhou (CN)

(72) Inventors: Chunxin Yang, San Jose, CA (US); Fuchun Li, Jiangsu (CN); Zenguang Li, Jiangsu (CN)

(73) Assignee: Suzhou Caring Medical Co., Ltd., Suzhou (CN)

( * ) Notice: Subject to any disclaimer, the term of this patent is extended or adjusted under 35 U.S.C. 154(b) by 824 days.

(21) Appl. No.: 14/678,658

(22) Filed: Apr. 3, 2015

(65) Prior Publication Data
US 2016/0287081 A1  Oct. 6, 2016

(51) Int. Cl.
*A61B 5/00* (2006.01)
*A61B 90/00* (2016.01)
*A61B 90/30* (2016.01)

(52) U.S. Cl.
CPC .......... *A61B 5/0071* (2013.01); *A61B 90/361* (2016.02); *A61B 2090/304* (2016.02); *A61B 2090/3612* (2016.02); *A61B 2090/373* (2016.02); *A61B 2505/05* (2013.01); *A61B 2562/0233* (2013.01)

(58) Field of Classification Search
CPC .. A61B 5/413; A61B 1/06; A61B 5/00; A61B 1/0646; A61B 1/00186; A61B 1/00; A61B 5/0084; A61B 1/307; A61B 5/0071; G01N 21/6428; G01N 21/64
See application file for complete search history.

(56) References Cited

U.S. PATENT DOCUMENTS 6,936,004 B2 * 8/2005 Utsui ................. A61B 1/00167
600/182
9,258,549 B2   2/2016 Dicarlo et al.
(Continued)

FOREIGN PATENT DOCUMENTS

CN    1419428 A    5/2003
CN   102370462 A   3/2012
(Continued)

OTHER PUBLICATIONS

Zettl, Herbert (2011). Television Production Handbook (11th ed.). Boston, MA: Wadsworth Cengage Learning.*
(Continued)

*Primary Examiner* — Christopher Koharski
*Assistant Examiner* — Helene Bor
(74) *Attorney, Agent, or Firm* — Kilpatrick Townsend & Stockton LLP

(57) ABSTRACT

A method of operating a fluorescent imaging system during an open surgery procedure includes concurrently illuminating a tissue with NIR excitation light and visible light, wherein NIR fluorescent light is emitted from the tissue and collecting the NIR fluorescent light and reflected visible light that is reflected from the tissue. The method also includes blocking at least a portion of the NIR excitation light reflected from the tissue and attenuating the reflected visible light. The method further includes imaging, using a camera, the NIR fluorescent light and the attenuated reflected visible light.

18 Claims, 4 Drawing Sheets

(56) References Cited

U.S. PATENT DOCUMENTS

| | | | |
|---|---|---|---|
| 9,277,205 B2 | 3/2016 | Zhao et al. | |
| 2004/0124791 A1* | 7/2004 | Takahashi | A61B 1/045 |
| | | | 315/297 |
| 2004/0152987 A1* | 8/2004 | Haisch | G01N 21/6428 |
| | | | 600/473 |
| 2004/0215060 A1* | 10/2004 | Ueno | A61B 1/00009 |
| | | | 600/160 |
| 2005/0059894 A1* | 3/2005 | Zeng | A61B 1/00055 |
| | | | 600/476 |
| 2005/0085732 A1* | 4/2005 | Sevick-Muraca | A61B 5/0059 |
| | | | 600/473 |
| 2005/0182321 A1 | 8/2005 | Frangioni | |
| 2005/0285038 A1* | 12/2005 | Frangioni | G01N 21/6456 |
| | | | 250/330 |
| 2006/0089554 A1* | 4/2006 | Ishihara | A61B 5/0071 |
| | | | 600/476 |
| 2006/0141633 A1* | 6/2006 | Balas | A61B 1/303 |
| | | | 436/164 |
| 2007/0276258 A1* | 11/2007 | Crane | A61B 5/742 |
| | | | 600/476 |
| 2008/0239070 A1* | 10/2008 | Westwick | A61B 1/045 |
| | | | 348/68 |
| 2009/0192349 A1 | 7/2009 | Berguer et al. | |
| 2010/0262017 A1* | 10/2010 | Frangioni | A61B 1/0005 |
| | | | 600/476 |
| 2011/0063427 A1 | 3/2011 | Fengler et al. | |
| 2013/0300836 A1 | 11/2013 | Zhao et al. | |
| 2013/0300837 A1 | 11/2013 | Dicarlo et al. | |
| 2013/0324858 A1 | 12/2013 | Xu et al. | |
| 2014/0187967 A1* | 7/2014 | Wood | A61B 5/0071 |
| | | | 600/473 |
| 2015/0018690 A1* | 1/2015 | Kang | A61B 5/418 |
| | | | 600/473 |

FOREIGN PATENT DOCUMENTS

| | | |
|---|---|---|
| CN | 107635451 A | 1/2018 |
| GB | 2493994 A | 2/2013 |
| WO | 2013096850 A1 | 6/2013 |
| WO | 2014176375 | 10/2014 |
| WO | 2016/160820 A1 | 10/2016 |

OTHER PUBLICATIONS

PCT/US2016/024735, "International Search Report and Written Opinion", dated Jul. 5, 2016, 9 pages.
International Preliminary Report on Patentability received in International Patent Application No. PCT/US2016/02735, dated Oct. 12, 2017. 8 pages.
Office Action received in Chinese Patent Application No. 201680019771.2, dated Jan. 28, 2019. Translation included. 13 pages.
Office Action received in Chinese Patent Application No. 201680019771.2, dated Aug. 21, 2019, 6 pages; Translation included.
China Patent Application No. 201680019771.2, Office Action, dated Nov. 3, 2020, 15 pages.

\* cited by examiner

METHOD AND APPARATUS FOR CONCURRENT IMAGING AT VISIBLE AND INFRARED WAVELENGTHS

STATEMENT AS TO RIGHTS TO INVENTIONS MADE UNDER FEDERALLY SPONSORED RESEARCH OR DEVELOPMENT

Not Applicable

BACKGROUND OF THE INVENTION

Near infrared (NIR) indocyanine green (ICG) fluorescence methods have been used in the field of medical diagnostics. For example, these methods have been used for detection of cancer tumors, navigation of the sentinel lymph node, and diagnosis of perfusion of tissues and organs. The ICG fluorescence method can be applied in several surgical procedures including skin and muscle transplants, gastrointestinal anastomosis, wound healing in general surgery, tumor clearance, and cystic resection.

A promising technique for detecting a lesion in a living body during open surgery procedures involves NIR fluorescent imaging, in which a fluorescent dye, for example, ICG fluorescent dye is administrated into a patient, excitation light at NIR wavelengths irradiates the target tissues in the patient, the fluorescent dye in the tissue emits fluorescent light at NIR wavelengths, which are longer than the wavelength of the excitation light, and an imaging system captures the NIR fluorescent light to generate a fluorescent image. Identification of the lesion is based on the intensity distribution of the fluorescent image.

Despite the progress made in NIR fluorescent imaging, there is a need in the art for improved methods and systems related to NIR fluorescent imaging, particularly for open field surgery applications.

SUMMARY OF THE INVENTION

The present invention relates generally to fluorescent imaging systems. More particularly, embodiments of the present invention relate to an apparatus and method for concurrent imaging of both NIR fluorescent light and visible light, for example, using a single image sensor or camera, in open surgery procedures.

According to an embodiment of the present invention, a fluorescent imaging system for concurrently imaging at both NIR and visible wavelengths is provided. The fluorescent imaging system includes a camera head, a controller and an image display device. The camera head radiates NIR excitation light and it detects NIR fluorescent light and visible light to generate an image. The controller is coupled to the camera head and the image display device. The controller controls the NIR excitation light source and the image sensors in the camera head. The image signal from the camera head is processed by the controller and displayed on the image display device.

According to another embodiment of the present invention, a method of operating a concurrently imaging system in NIR and visible wavelengths for fluorescence diagnostic during open surgery is provided. The method includes administering a fluorescent dye to a tissue, illuminating the tissue with NIR excitation light and visible light concurrently, imaging the tissue using an image sensor, and balancing the intensity of the NIR excitation light and the intensity of the visible light so that the contrast between the fluorescent regions and the non-fluorescent regions on the image are suitable for observation and lesion identification.

In a specific embodiment, the camera head of the fluorescent imaging system for concurrently imaging at both NIR and visible wavelengths includes a NIR excitation light source, a camera, a filter that blocks NIR excitation light from entering the camera, and an attenuator to decrease the intensity of visible light detected by the camera. The NIR light source can be a solid state light source such as laser diode or LED. The camera can be a single chip CCD or CMOS camera or a 3-chip CCD or CMOS camera. The irradiation path of the NIR excitation light can be either co-axial or off-axis with respect to the imaging path. The intensity of the NIR excitation light can be adjusted by controlling the drive current of the NIR excitation light source.

According to a specific embodiment of the present invention, a method of operating a fluorescent imaging system for open surgery procedures includes concurrently illuminating a tissue with near-infrared excitation light and visible light, imaging the tissue using a camera, attenuating an intensity of the visible light and adjusting an intensity of the NIR excitation light to achieve a suitable contrast between fluorescent and non-fluorescent regions on the image.

According to a particular embodiment of the present invention, a method of operating an imaging system is provided. The method includes applying a fluorescent dye to a target tissue and providing an NIR excitation light source operable to produce NIR excitation light having an excitation wavelength. The method also includes concurrently illuminating the target tissue using the NIR excitation light and visible light having visible wavelengths, collecting fluorescent emission from the target tissue, and collecting visible light reflected from the target tissue. The method further includes passing the collected fluorescent emission and the reflected visible light through an optical system comprising a first filter operable to reduce an intensity of light at the excitation wavelength and a second filter operable to reduce an intensity of light at the visible wavelengths. Additionally, the method includes concurrently detecting the fluorescent emission and filtered visible light reflected from the target tissue to form an image of the target tissue and adjusting the NIR excitation light source to modify a contrast of the image of the target tissue.

According to another particular embodiment of the present invention, a fluorescent imaging system for concurrently imaging at both NIR and visible wavelengths is provided. The fluorescent imaging system includes a camera head including a NIR light source operable to generate NIR excitation light and a camera operable to detect NIR fluorescent light and visible light concurrently. The fluorescent imaging system also includes a controller coupled to the camera head and an image display device.

According to yet another particular embodiment of the present invention, a method of operating a fluorescent imaging system during an open surgery procedure is provided. The method includes concurrently illuminating a tissue with NIR excitation light and visible light, wherein NIR fluorescent light is emitted from the tissue and collecting the NIR fluorescent light and reflected visible light that is reflected from the tissue. The method also includes blocking at least a portion of the NIR excitation light reflected from the tissue and attenuating the reflected visible light. The method further includes imaging, using a camera, the NIR fluorescent light and the attenuated reflected visible light.

Numerous benefits are achieved by way of the present invention over other known methods for imaging in both NIR and visible wavelengths. For example, some of the known methods utilize time sequentially illumination and imaging in NIR and visible wavelengths, and some other methods utilize splitting NIR and visible wavelengths in space and separately detecting the NIR and visible wavelengths with multiple image sensors. In contrast with these techniques, embodiments of the present invention utilize concurrent illumination and imaging in both NIR and visible wavelengths to effectively provide information for medical procedures. These and other embodiments of the invention along with many of its advantages and features are described in more detail in conjunction with the text below and attached figures.

DETAILED DESCRIPTION OF SPECIFIC EMBODIMENTS

NIR fluorescence methods used for medical diagnostics utilize an exogenous fluorescent dye such as indocyanine green (ICG) that can be administered to the patient and will combine with the tissue to be observed. In addition to IGC, other suitable dyes, such as methylene blue can be used as a source of fluorescent emission. Excitation light with wavelengths in the NIR spectrum is then used to irradiate the tissue and excite the fluorescent dye in the tissue. The resulting fluorescent light is detected at NIR wavelengths longer than the wavelength of the excitation light based on the Stokes shift. The fluorescence quantum yields drive the efficiency of the fluorescence process, which is normally low. As a result, the intensity of the NIR fluorescent light is generally very weak compared to the intensity of the NIR excitation light. Therefore, in order to observe the fluorescence image, a filter is typically utilized to block the NIR excitation light from reaching the image sensor.

A CCD or CMOS image sensor typically has a spectral response from 200 nm to 1100 nm, allowing the image sensor to capture light for imaging in both the NIR and the visible regions of the spectrum. However, the spectral response of an image sensor in the NIR spectrum is only 10%-30% of the peak response in the visible portion of the spectrum. Thus embodiments of the present invention, which provide fluorescent imaging apparatus incorporating both NIR fluorescent light and visible light imaging, attenuate the intensity of the visible light so that the visible light does not overwhelm the image sensor.

Conventional NIR fluorescent imaging systems detect NIR wavelengths and block visible wavelengths in order to achieve the desired signal-to-noise ratio. Accordingly, conventional systems only display the fluorescent regions, with the non-fluorescent regions appearing as dark areas. According to embodiments of the present invention, an imaging technique is provided that enables display of both the fluorescent regions for identifying the lesions and the non-fluorescent regions for locating the lesions. Accordingly, the systems described herein perform imaging at both NIR and visible wavelengths concurrently.

Figure 1:
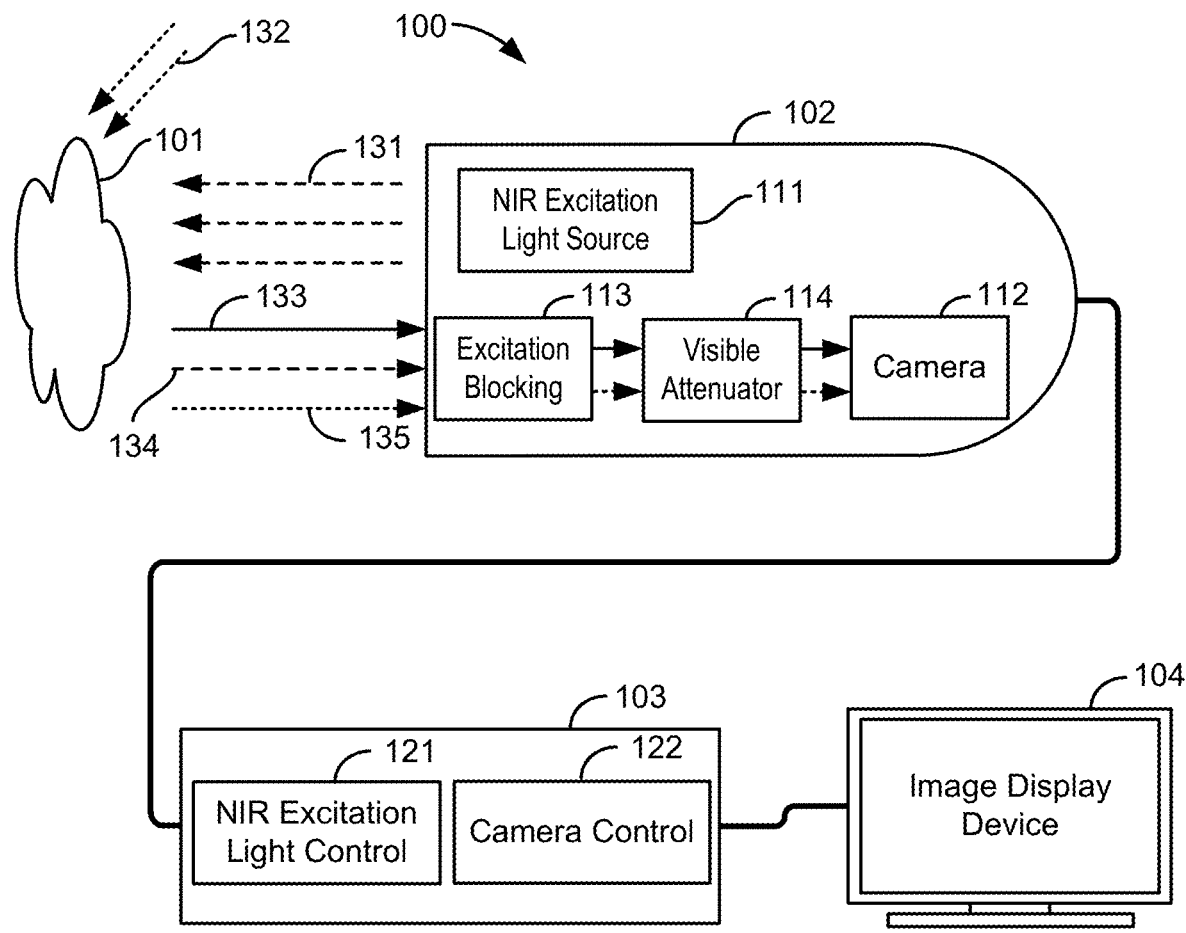
FIG. 1 is a simplified schematic diagram of a fluorescent imaging system for concurrent imaging in both the NIR and visible wavelengths according to an embodiment of the present invention.

FIG. 1 is a simplified schematic diagram of a fluorescent imaging system for concurrent imaging in both the NIR and visible wavelengths according to an embodiment of the present invention. The basic schematic block diagram of a fluorescent imaging system for concurrent imaging in both the NIR and visible wavelengths as illustrated in FIG. 1 is exemplary and not intended to limit the present invention. A number of embodiments of the present invention that include imaging both NIR and visible light at the same time are included within the scope of the invention. As described herein, embodiments of the present invention are particularly useful for open field surgery, in which the medical personnel (e.g., the doctor) do not need a visible video image from an endoscope to obtain a visible image of the surgery area and tissue under examination because of the exposure of the tissue to ambient light.

The fluorescent imaging system 100 comprises a camera head 102, a controller 103 and an image display device 104. The camera head 102, described more fully below, includes a NIR excitation light source 111 and a camera 112. The NIR excitation light source 111 generates excitation light 131 with wavelengths in a first NIR spectrum (e.g., 790 nm-820 nm, in particular in the vicinity around 800 nm). The NIR excitation light 131 irradiates target tissue 101. Visible light 132 (e.g., with wavelengths in the range of 400 nm-700 nm) is provided by conventional surgical lamps or other suitable sources for general illumination. Thus, the target tissue 101 is illuminated concurrently by NIR excitation light 131 and visible light 132. Accordingly, fluorescent light and a visible background are produced during system operation.

The camera head 102 receives fluorescent light 133 with wavelengths in a second NIR spectrum (e.g., 830 nm-900 nm) excited from the target tissue 101. The camera head 102 also receives NIR excitation light 134 reflected from the target tissue 101 as well as visible light 135 reflected from the target tissue 101. The camera head 102 includes an excitation blocking filter 113 (i.e., a notch filter operable to block light in the first NIR spectrum) to block reflected NIR excitation light 134. The camera head 102 also includes a visible light attenuator 114 to decrease the intensity of reflected visible light 135. In some embodiments, the position of the excitation blocking filter 113 and the visible light attenuator 114 with respect to the optical path can be interchanged, for example, with the visible attenuation occurring before the attenuation of the reflected NIR excitation light. In some embodiments, the excitation blocking filter 113 and the visible light attenuator 114 are implemented by a single optical component. The camera 112 detects the NIR fluorescent light 113 that passes through the filters and the attenuated visible light and generates image signals.

The controller 103 is coupled to the camera head 102. The functions of the controller 103 include NIR excitation light control 121 for adjusting the intensity of the NIR excitation light and camera control 122 for adjusting camera configurations. The image signals from the camera head 102 are processed by the controller 103 and are eventually displayed on the image display device 104.

In some embodiments, multiple fluorescent dyes and multiple excitation wavelengths are utilized, with optical filters (i.e., notch filters) utilized in the imaging optical path that block the excitation light from each of the excitation sources from passing to the image sensor. An optical filter with multiple notches (e.g. dual notch) having low transmission or multiple single notch optical filters can be utilized in these embodiments. NIR fluorescent light and reflected visible light from the target tissue (at multiple fluorescent wavelengths in the case of multiple fluorescent dyes) is transmitted through the optical filter(s) for subsequent detection at the image sensor. Since two dyes can have different responses to the excitation light, embodiments provide benefits not available using conventional techniques. In some implementations, the NIR excitation light source provides excitation light peaking at multiple wavelengths in order to produce efficient fluorescence from each of the fluorescent dyes. Moreover, in some embodiments, the NIR excitation light source is controllable to produce light having a single and adjustable excitation peak, multiple excitation peaks, or the like, depending on the fluorescent dyes that are being utilized during a particular medical procedure.

Embodiments of the present invention provide for concurrent illumination using both NIR excitation light and visible light as well as concurrent imaging of both NIR fluorescent light emitted by the fluorescent dye, which can be associated with the target tissue, and the visible light reflected from the target tissue. This concurrent or simultaneous imaging of both NIR and visible light using a single camera contrasts with conventional systems that utilize time sequential imaging at these differing wavelengths or an optical system that splits the different wavelengths to direct the different wavelengths to different image sensors.

Figure 2:
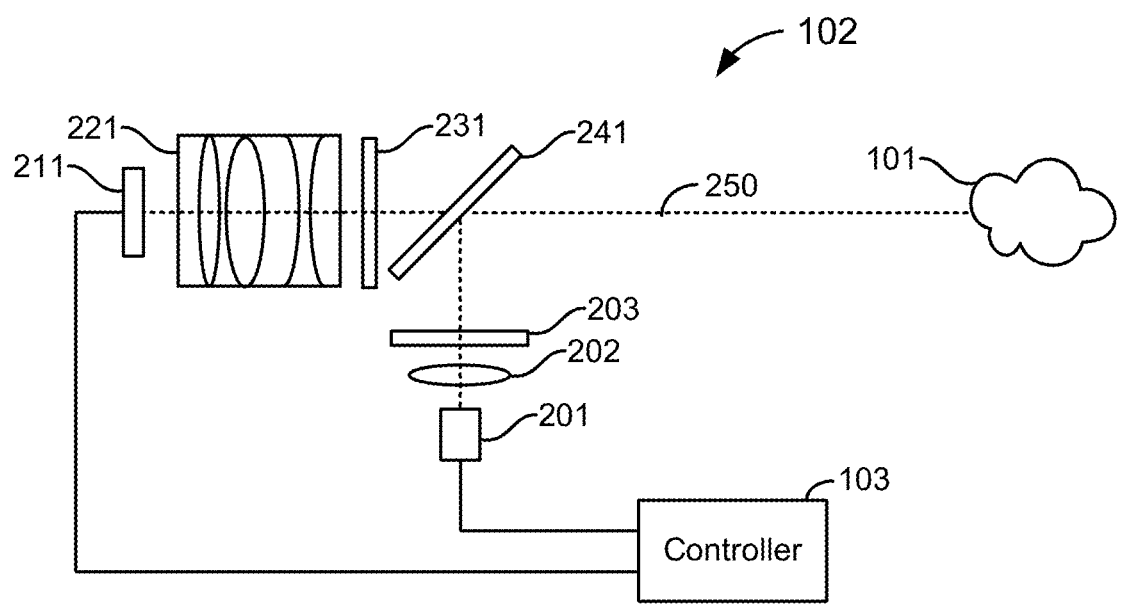
FIG. 2 is a simplified schematic diagram of a first embodiment of a camera head for a fluorescent imaging system according to an embodiment of the present invention.

FIG. 2 is a simplified schematic diagram of a first embodiment of a camera head for a fluorescent imaging system according to an embodiment of the present invention. Referring to FIG. 2, the camera head 102 includes a light source and a camera in a coaxial configuration in which the NIR excitation light and the light used for imaging propagate along a common axis. A NIR light source 201 generates excitation light with wavelengths in the first NIR spectrum (e.g., 790 nm-820 nm). In some embodiments, the NIR light source 201 is a semiconductor laser, but LEDs and the like can be utilized. The output of the NIR light source 201 is shaped by a beam shaping lens 202 to achieve desired beam diameter and diverging angle. The shaped NIR excitation light passes through a laser-line filter 203 that is characterized by a very narrow passband (e.g., 10 nm wide). The laser-line filter 203 transmits the desired excitation wavelengths while suppressing side-band radiation. The intensity of the NIR excitation light is controlled by the controller 103 through adjustment of the driving current of the NIR light source 201 in some embodiments.

The camera in the first embodiment of the camera head is a single chip camera which includes one image sensor 211 and a camera lens 221. The image sensor 211 can be CCD, CMOS, or other suitable sensors to provide monochromatic or color output. The camera lens 221 focuses light onto the image sensor 211. A visible light neutral density filter 231 is placed in a position optically upstream of the camera lens 221. The visible light neutral density filter 231 (or other suitable visible light attenuator) is an optical filter that attenuates the intensity of visible light (e.g., wavelengths from 400 nm to 700 nm) reflected from the target tissue 101. As discussed herein, the reflected visible light is attenuated so that the visible light does not swamp the signal associated with the NIR fluorescent light. In other embodiments, the visible light neutral density filter 231 can be assembled into the camera lens 221 or be placed after the camera lens 221. The image sensor 211 is connected to the controller 103 and its gain, exposure time, and the like is controllable.

The first embodiment of a camera head for a fluorescent imaging system arranges the irradiation path co-axially with the imaging path. Referring to FIG. 2, an excitation blocking filter 241 is utilized as a mirror to direct the NIR excitation light toward the target tissue 101 and along imaging path 250. The excitation blocking filter 241 is typically a notch filter that reflects excitation light with wavelengths in the first NIR spectrum (e.g., 790 nm-820 nm) and transmits fluorescent light with wavelengths in the second NIR spectrum (e.g., 830 nm-900 nm) and visible light with wavelengths from 400 nm to 700 nm. In the illustrated embodiment, the excitation blocking filter 241 is designed to work at an incident angle of 45°. In other embodiments, the excitation blocking filter may work at an incident angle of less than or greater than 45°. As illustrated, the NIR excitation light is incident on the excitation blocking filter 241 with a center incident angle of 45°. The NIR excitation light is reflected by the excitation blocking filter and the direction of the NIR excitation light (also referred to as the irradiation path) is aligned with the imaging path 250. The excitation blocking filter 241 also blocks the NIR excitation light reflected from the tissue 101 so the NIR excitation light is prevented from entering the camera. Referring to FIG. 1, excitation blocking filter 113 corresponds to excitation blocking filter 241 and visible light attenuator 114 corresponds to visible light neutral density filter 231. In some embodiments, excitation blocking filter 241 is a dichroic filter that reflects light in the first NIR spectrum and passes light in the second NIR spectrum. Although excitation blocking filter 241 and visible light neutral density filter 231 are illustrated as separate optical elements in FIG. 2, this is not required by the present invention and the functionality of these elements can be integrated into a single optical element (i.e., a single dichroic filter) in some embodiments. One of ordinary skill in the art would recognize many variations, modifications, and alternatives.

Embodiments of the present invention provide concurrent imaging of both NIR fluorescent emission as well as reflected visible light using a single camera to image both signals. In contrast with systems that separate visible and infrared light for detection using separate sensors, embodiments combine the detection process using a single sensor.

Figure 3:
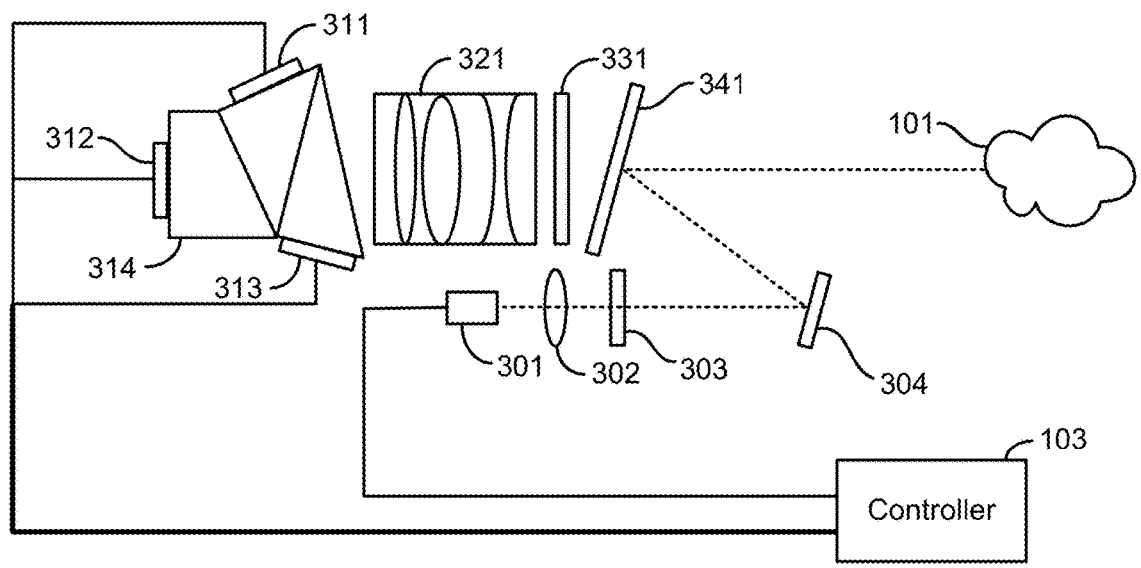
FIG. 3 is a simplified schematic diagram of a second embodiment of a camera head for a fluorescent imaging system according to an embodiment of the present invention.

FIG. 3 is a simplified schematic diagram of a second embodiment of a camera head for a fluorescent imaging system according to an embodiment of the present invention. In the alternative embodiment illustrated in FIG. 3, the camera head includes a light source and a camera. A NIR excitation light source 301 generates excitation light with wavelengths in the first NIR spectrum (e.g., 790 nm-820 nm). In a manner similar to the embodiment depicted in FIG. 2, a beam shaping lens 302 shapes the beam profile of the NIR excitation light, and a laser-line filter 303, which is characterized by a narrow passband (e.g., 10 nm), is utilized to transmit the desired excitation wavelengths while suppressing side-band radiation. Depending on the arrangement, a mirror 304 may be utilized to change the direction of the NIR excitation light in compact designs.

The camera in the second embodiment of the camera head is a 3-panel camera, that is, a 3-chip camera that includes a red image sensor 311, a green image sensor 312, a blue image sensor 313, a prism 314, and a camera lens 321. Depending on the wavelengths of the incoming light, the prism 314 splits the light into red, green, and blue colors, each color directed onto one image sensor. The fluorescent light with wavelengths in the NIR spectrum will be focused onto one or more of the red image sensor 311, the green image sensor 312, or the blue image sensor 313. The optical path lengths from the camera lens 321 to the three image sensors are identical in some embodiments. The prism 314 illustrated in FIG. 3 is an example of an optical component useful for color splitting. However, there are many variations of the optical component including prisms and filters.

Although the visible image sensors typically utilize filters to block radiation outside the color range associated with the sensor, these filters are often designed to work in the visible range of the spectrum. Accordingly, the NIR fluorescent emission, for example, at 800 nm, can be detected on one or more of the visible image sensors if the various filters do not block radiation at these infrared wavelengths. As an example, 800 nm radiation incident on some color cameras can produce a yellow image since the red image sensor and the green image sensor can receive the 800 nm light, which then results in a yellow color due to the combination of red and green light.

The camera lens 321 focuses light onto the three image sensors. A visible light neutral density filter 331 is placed upstream of the camera lens 321. The visible light neutral density filter 331 is an optical filter that attenuates the intensity of visible light with wavelengths from 400 nm to 700 nm. In other embodiments, the visible light neutral density filter 331 can be assembled into the camera lens 321 or be placed downstream of the camera lens 321.

The second embodiment of a camera head for a fluorescent imaging system arranges the irradiation path co-axially with the imaging path. Referring to FIG. 3, an excitation blocking filter 341 is utilized to direct the NIR excitation light to propagate along the imaging path. The excitation blocking filter 341 is typically a notch filter that blocks excitation light with wavelengths in the first NIR spectrum (e.g., 790 nm-820 nm) and transmits fluorescent light with wavelengths in the second NIR spectrum (e.g., 830 nm-900 nm) and visible light with wavelengths from 400 nm to 700 nm. In this embodiment, the excitation blocking filter 341 is designed to work at an incident angle of 15°. In other embodiment, the optical filter can have a different incident angle. The NIR excitation light is incident on the excitation blocking filter 341 with a center incident angle of 15°. The NIR excitation light is reflected by the excitation blocking filter 341, and the direction of the NIR excitation light (i.e., the irradiation path) is aligned with the imaging path. The excitation blocking filter 341 also blocks the NIR excitation light reflected from the tissue so that the NIR excitation light is prevented from entering the camera.

Figure 4:
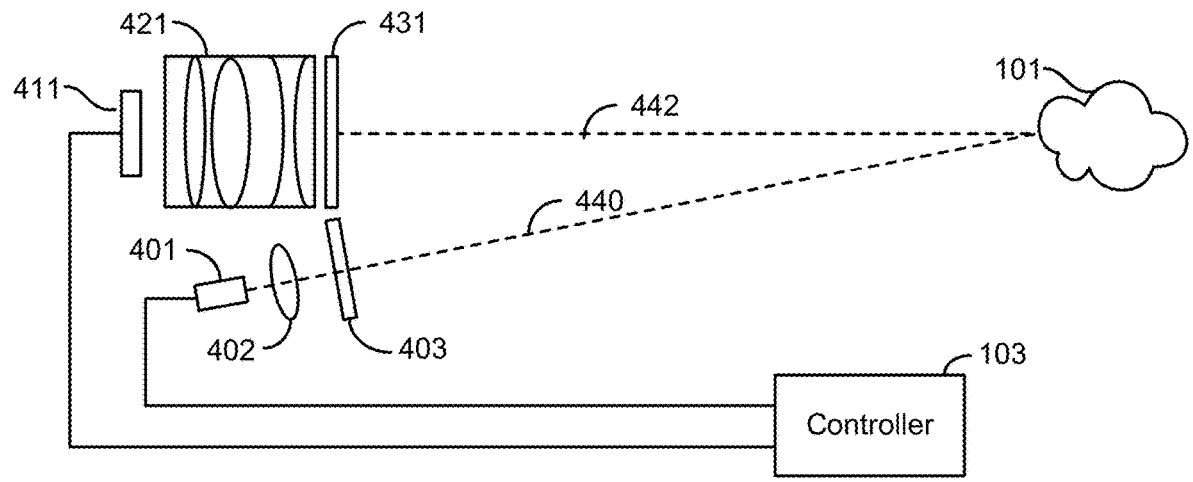
FIG. 4 is a simplified schematic diagram of a third embodiment of a camera head for a fluorescent imaging system according to an embodiment of the present invention.

FIG. 4 is a simplified schematic diagram of a third embodiment of a camera head for a fluorescent imaging system according to an embodiment of the present invention. Referring to FIG. 4, the camera head includes a light source and a camera in an off-axis configuration. The light source includes a NIR excitation light source 401 which generates excitation light with wavelengths in the first NIR spectrum (e.g., 790 nm-820 nm), a beam shaping lens 402 for beam profile adjustment and a laser-line filter 403, which transmits the desired excitation wavelengths while suppressing side-band radiation. The intensity of the NIR excitation light is controlled by the controller 103 through adjustment of the driving current of the NIR light source 401.

The camera in the third embodiment of the camera head is a single chip camera that includes one image sensor 411 and a camera lens 421. The image sensor 411 can be CMOS or CCD. The camera lens 421 focuses light onto the image sensor 411. An optical filter 431 (which can be implemented as a filter set) is placed optically upstream of the camera lens 421. The optical filter 431 blocks the excitation light with wavelengths in the first NIR spectrum (e.g., 790 nm-820 nm), transmits fluorescent light with wavelengths in the second NIR spectrum (e.g., 830 nm-900 nm), and attenuates visible light with wavelengths from 400 nm to 700 nm. In other embodiments, the optical filter 431 can be assembled into the camera lens 421 or be placed downstream of the camera lens 421. The image sensor 411 is connected by the controller 103 so its gain, exposure time, and the like is controllable. In other embodiments, the camera can be a 3-chip camera as described in the second embodiment of the camera head in relation to FIG. 3.

The third embodiment of a camera head for a fluorescent imaging system arranges the irradiation path off-axis with the imaging path. Referring to FIG. 4, the direction of the NIR excitation light along the excitation path 440 is different from the imaging path 442. The NIR excitation light is orientated in such a way that there is a small angle between the irradiation path and the imaging path. This angle is calculated so that at the position of the target tissue, the NIR excitation light irradiate an area approximately the same as the field of view of the camera lens 421.

Figure 5:
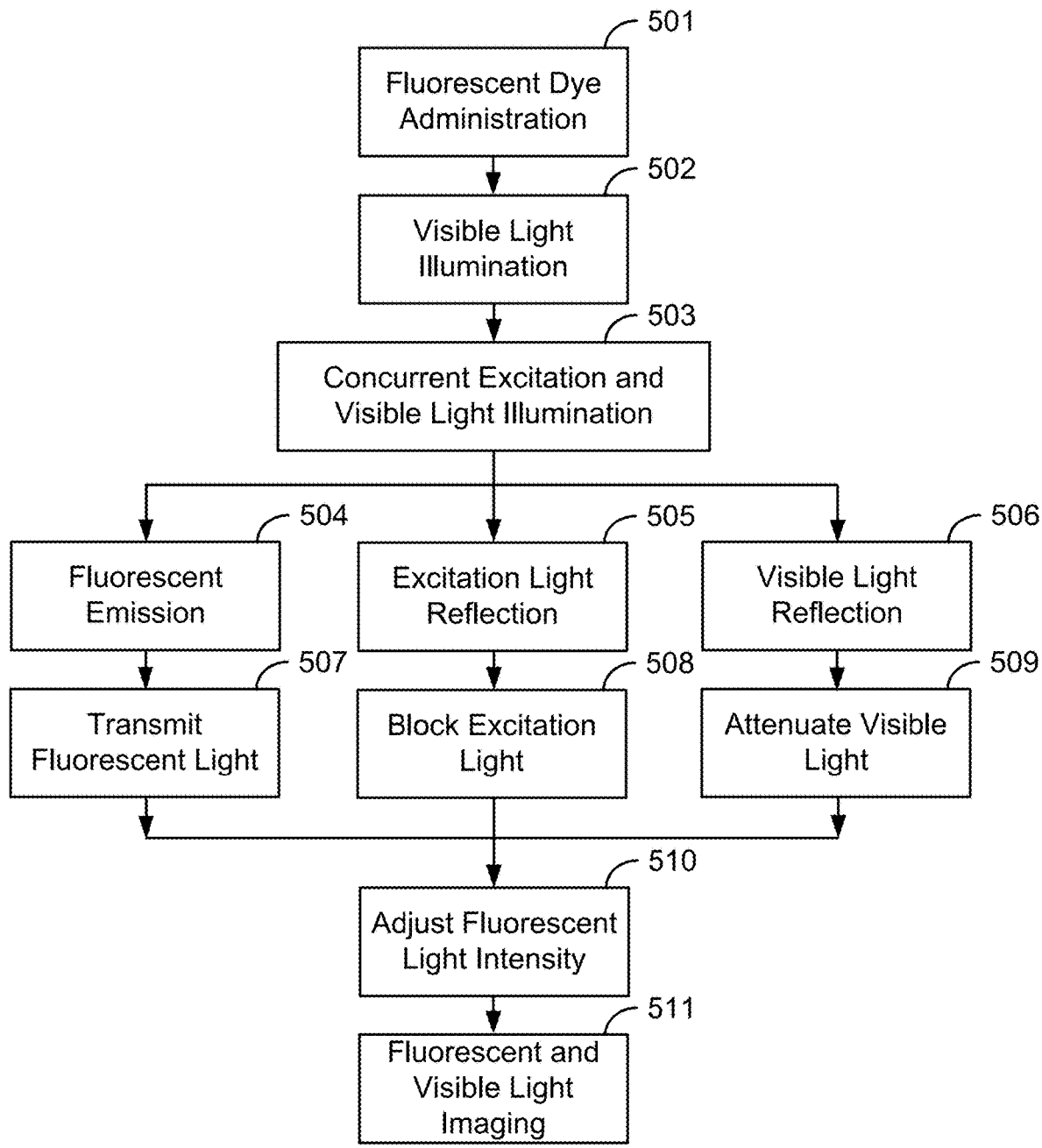
FIG. 5 is a simplified flowchart illustrating a method of operating a fluorescent imaging system for detecting a lesion during open surgery procedures according to an embodiment of the present invention.

FIG. 5 is a simplified flowchart illustrating a method of operating a fluorescent imaging system with concurrent imaging according to an embodiment of the present invention. Because embodiments of the present invention image both NIR fluorescent light and reflected visible light concurrently or simultaneously, the systems described herein balance the intensity of the NIR fluorescent light and the intensity of visible light to provide a suitable contrast between the fluorescent regions and the non-fluorescent regions in the image.

As an example, the fluorescent imaging system depicted in FIG. 1 can utilize the process illustrated in FIG. 5 for concurrent imaging of NIR fluorescent light and visible light during an open surgery procedure. The method includes, for example, prior to an open surgery procedure, administering a fluorescent dye to the target tissue (501). During the entire surgery procedure in some embodiments, visible light illumination is applied using surgical lamps or other suitable light sources in the surgical suite (502). Observation with eyes under visible light illumination is utilized for the majority of the duration of the procedure and no imaging apparatus is needed. The fluorescent imaging system is applied, for example, when fluorescent observation is needed for identification of lesions.

When the fluorescent imaging system is activated, the camera head irradiates the target tissue with NIR excitation light. Meanwhile, visible light from surgical lamps also illuminates the target tissue concurrently (503). The NIR excitation light excites the fluorescent dye in the target tissue and generates NIR fluorescent light (504). The target tissue reflects some NIR excitation light and some visible light (505, 506). The camera head processes the NIR fluorescent light, the reflected NIR excitation light, and the reflected visible light differently.

The NIR fluorescent light is transmitted so that the camera detects the NIR fluorescent light (507), for instance, with as high an intensity as possible. The NIR excitation light is blocked utilizing an excitation blocking filter in the camera head so that the camera detects no or substantially no NIR excitation light (508). As discussed herein, different embodiments can block the NIR excitation light in various ways. The reflected visible light is attenuated utilizing a neutral density filter working at visible wavelengths so that the camera detects a low intensity of visible light compared to the total intensity of reflected visible light (509). The intensity of the NIR fluorescent light at the camera is adjusted through control of the intensity of the NIR excitation light used for irradiation (510), for example, by modifying the intensity of the NIR excitation light source 111. Accordingly, the camera concurrently images the NIR fluorescent light and the reflected visible light (after attenuation) and forms an image including both fluorescent regions and non-fluorescent regions (511).

The fluorescent regions contain signals that result from both NIR fluorescent light and reflected visible light. The fluorescent observation focuses on the fluorescent regions to identify lesions. The non-fluorescent regions only contain signals that result from the visible light. The ability to visualize tissue in the non-fluorescent regions helps to locate lesions. For preferable observation conditions, the attenuation ratio of the visible light is carefully selected to achieve a predetermined (e.g., maximum) contrast between the fluorescent regions and non-fluorescent regions. In some embodiments, if the brightness of the fluorescent regions on the image needs to be increased or decreased, the controller can be used to adjust the intensity of the NIR excitation light and thereby control the intensity of the NIR fluorescent light (510).

It should be appreciated that the specific steps illustrated in FIG. 5 provide a particular method of operating a fluorescent imaging system with concurrent imaging according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 6A:
FIG. 6A is an image of tissue with visible illumination according to an embodiment of the present invention.

FIG. 6A is an image of tissue with visible illumination according to an embodiment of the present invention. In the image shown in FIG. 6A, the tissue is illuminated with visible light, enabling the surgeon to visualize the area to be analyzed. This visible imagery, which can be captured in color using a regular camera, provides details of the physical state of the tissue.

Figure 6B:
FIG. 6B is an image of the tissue illustrated in FIG. 6A with concurrent visible illumination and NIR fluorescent emission according to an embodiment of the present invention.

FIG. 6B is an image of the tissue illustrated in FIG. 6A with concurrent visible illumination and NIR fluorescent emission according to an embodiment of the present invention. As shown in FIG. 6B, the fluorescent emission provides additional information not available using the visible image. Because the fluorescent emission and the reflected visible light is captured concurrently, the fluorescent emission can be referenced to the physical tissue, enabling surgery or other medical techniques to be applied.

It is also understood that the examples and embodiments described herein are for illustrative purposes only and that various modifications or changes in light thereof will be suggested to persons skilled in the art and are to be included within the spirit and purview of this application and cope of the appended claims.

What is claimed is:

1. A method of operating an imaging system, the method comprising:
    applying a fluorescent dye to a target tissue;
    providing a near infrared (NIR) excitation light source operable to produce NIR excitation light having an excitation wavelength;
    providing a surgical lamp operable to produce continuous visible illumination light having visible wavelengths;
    concurrently illuminating the target tissue with the NIR excitation light produced by the NIR excitation light source and the continuous visible illumination light produced using the surgical lamp;
    collecting fluorescent emission from the target tissue;
    collecting visible light reflected from the target tissue;
    passing the collected fluorescent emission and the reflected visible light through the imaging system, wherein the imaging system comprises:
        a single image sensor;
        a first filter operable to reduce an intensity of light at the excitation wavelength; and
        a visible light attenuator disposed between the target tissue and the single image sensor and operable to reduce an intensity of the reflected visible light;
    forming an image of the target tissue using the single image sensor by concurrently detecting the fluorescent emission and attenuated reflected visible light; and
    adjusting the NIR excitation light source to modify a contrast of the image of the target tissue.

2. The method of claim 1 wherein the first filter is operable to block substantially all light at the excitation wavelength.

3. The method of claim 1 wherein the first filter and the visible light attenuator are integrated as a single dichroic filter.

4. The method of claim 1 wherein the NIR excitation light source comprises a diode laser or light emitting diode.

5. The method of claim 1 wherein the NIR excitation light, the fluorescent emission, and the reflected visible light propagate along a coaxial propagation path.

6. The method of claim 1 wherein the single image sensor comprises a single chip CCD or CMOS sensor.

7. A fluorescent imaging system for concurrently imaging at both NIR and visible wavelengths, the fluorescent imaging system comprising:
    a camera head;
    a surgical lamp operable to provide continuous visible illumination light to illuminate a tissue;
    a controller coupled to the camera head; and
    an image display device,
    wherein the camera head comprises:
        an NIR light source operable to generate NIR excitation light to illuminate the tissue, wherein NIR fluorescent light is emitted from the tissue;
        a first filter operable to reduce an intensity of the NIR excitation light;
        a visible light attenuator operable to reduce an intensity of reflected visible light; and
        a single image sensor operable to detect an intensity of the NIR fluorescent light and the intensity of the reflected visible light concurrently, wherein the visible light attenuator is disposed between the tissue and the single image sensor.

8. The fluorescent imaging system of claim 7 wherein the NIR light source comprises at least one solid state light source and the single image sensor comprises a single chip CCD or CMOS sensor.

9. The fluorescent imaging system of claim 7 wherein the controller is operable to vary an intensity of the NIR excitation light.

10. The fluorescent imaging system of claim 7 wherein:
the NIR excitation light propagates along an illumination path;
the NIR fluorescent light propagates along an imaging path; and
the reflected visible light propagates along the imaging path, wherein the illumination path and the imaging path are coaxial.

11. The fluorescent imaging system of claim 7 wherein:
the NIR excitation light propagates along an illumination path;
the NIR fluorescent light propagates along an imaging path; and
the reflected visible light propagates along the imaging path, wherein the illumination path and the imaging path are oriented at an angle to each other.

12. A method of operating a fluorescent imaging system during an open surgery procedure, the method comprising:
concurrently illuminating a tissue with near infrared (NIR) excitation light provided by a NIR light source and continuous visible light provided by a surgical lamp, wherein NIR fluorescent light is emitted from the tissue;
collecting the NIR fluorescent light and reflected visible light that is reflected from the tissue;
blocking at least a portion of the NIR excitation light reflected from the tissue by a first filter;
attenuating the reflected visible light by a visible light attenuator disposed between the tissue and a single image sensor; and
concurrently imaging, using the single image sensor, the NIR fluorescent light and the attenuated reflected visible light.

13. The method of claim 12 wherein the at least a portion of the NIR excitation light is substantially all of the NIR excitation light.

14. The method of claim 12 further comprising adjusting an intensity of the NIR excitation light to modify a contrast between the NIR fluorescent light and the attenuated reflected visible light.

15. The method of claim 14 wherein adjusting the intensity of the NIR excitation light is performed by a controller coupled to the single image sensor.

16. The method of claim 12 wherein at least a portion of the tissue is exposed to a fluorescent dye.

17. The method of claim 12 wherein the NIR light source is a component of the fluorescent imaging system.

18. The method of claim 12 wherein the single image sensor comprises a single chip CCD or CMOS sensor.

* * * * *